United States Patent [19]

Becker et al.

[11] 4,178,329
[45] Dec. 11, 1979

[54] PLASTICS MATERIAL HAVING AN IMPROVED BLOOD TOLERANCE

[75] Inventors: Udo Becker, Marburg an der Lahn; Karlheinz Burg, Wiesbaden; Johann P. Fischer, Königstein; Norbert Heimburger, Marburg an der Lahn, all of Fed. Rep. of Germany

[73] Assignee: Hoechst Aktiengesellschaft, Frankfurt, Fed. Rep. of Germany

[21] Appl. No.: 902,901

[22] Filed: May 5, 1978

[30] Foreign Application Priority Data

Nov. 18, 1977 [DE] Fed. Rep. of Germany ....... 2751528

[51] Int. Cl.$^2$ ............................................. C08F 255/02
[52] U.S. Cl. ............................................ 525/77; 3/1.4
[58] Field of Search ................... 260/878 R, 879, 884; 3/1.4; 424/33, 78, 81

[56] References Cited

U.S. PATENT DOCUMENTS

| | | | |
|---|---|---|---|
| 2,733,228 | 1/1956 | Salyer et al. | 260/878 R |
| 2,945,836 | 7/1960 | Salyer et al. | 260/878 R |
| 3,068,187 | 12/1962 | Bolstad et al. | 260/878 R |
| 3,093,615 | 6/1963 | Bonvicini et al. | 260/878 R |
| 3,322,712 | 5/1967 | Gardner et al. | 260/878 R |
| 3,637,614 | 1/1972 | Greenwood | 260/878 R |
| 3,663,288 | 5/1972 | Miller | 3/1.4 |
| 3,839,743 | 10/1974 | Schwarcz | 3/1.4 |
| 3,868,408 | 2/1975 | Holland et al. | 260/884 |
| 3,981,958 | 9/1976 | Nakashima et al. | 260/878 R |
| 4,065,522 | 12/1977 | Myers et al. | 260/879 |

FOREIGN PATENT DOCUMENTS

| | | | |
|---|---|---|---|
| 47-23426 | 6/1972 | Japan | 260/878 R |
| 48-33995 | 10/1973 | Japan | 260/878 R |

*Primary Examiner*—Paul R. Michl
*Attorney, Agent, or Firm*—Curtis, Morris & Safford

[57] ABSTRACT

What is disclosed is a plastics material adaptable to biomedical uses, the surface of which material at least partially consists of a graft copolymer having a hydrocarbon main chain and side chains grafted thereon, said side chains being polymers comprising at least one vinyl monomer selected from the group consisting of acrylic acid esters of the formula $$CF_3-(CF_2)_x-(CH_2)_y-O-CO-CH=CH_2,$$

where x is an integer from 3 to 16 and y is an integer from 1 to 12, vinylene carbonate, N-vinyl alkylamides of the formula

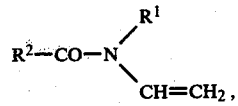

wherein $R^1$ and $R^2$ are the same or different and each is hydrogen or alkyl having 1 to 6 carbon atoms.

7 Claims, No Drawings

PLASTICS MATERIAL HAVING AN IMPROVED BLOOD TOLERANCE

The present invention relates to a plastics material having an improved blood tolerance.

It is known that plastics materials may lead to blood coagulation in varying intensity depending on their nature and on their surface structure; thus, a biochemical use of these plastics in this state is not possible. It is further known that an improvement of the blood tolerance of plastics surfaces may be achieved by incorporating hydrophobic groups, for example, methyl groups, or hydrophilic groups, for example hydroxyl groups and fluoroalkyl groups, or groups which have a negative charge, for example carboxylate groups, into the plastics composition (cf. German Offenlegungsschrift No. 25 41 527). These groups may be incorporated into the plastics substrate inter alia by grafting a monomer which contains the corresponding group onto the substrate. Additionally, a biologically active substance, for example heparin, may be combined with the graft polymer (cf. German Offenlegungsschrift No. 23 26 963).

It was the object of the present invention to develop a material based on a plastics composition which should be thermoplastically moldable on the one hand and on the other hand have athrombogenic properties and, consequently, be appropriate for biomedical use.

The present invention, consequently, provides a plastics material having an improved blood tolerance, characterized by the fact that its surface, which comes into contact with the blood, consists of a graft polymer which is composed of a hydrocarbon main chain and grafted hydrocarbon side chains, the latter possessing functional groups containing oxygen, sulfur, fluorine and/or nitrogen atoms.

The present invention moreover provides a process for the manufacture of a plastics material, which comprises polymerizing at least one vinyl monomer which possesses an oxygen, sulfur, fluorine and/or nitrogen atom-containing functional group, in the presence of a macromolecular aliphatic hydrocarbon under known conditions and optionally hydrolyzing the formed graft polymer.

The graft polymer is a macromolecular, branched, aliphatic hydrocarbon carrying functional groups in the side chains. The graft degree is generally in the range of from 0.01 to 80%, preferably of from 0.1 to 10%. By the term "graft degree" there is to be understood the portion by weight in percent of the side chains of the graft copolymer, calculated on the sum of polymer substrate and grafted vinyl monomers. The graft degree is usually determined by infrared spectrometry of the polymer material concerned.

The polymer substrate may be a macromolecular aliphatic hydrocarbon which is preferably linear or branched by lower alkyl radicals. The polymer substrate is preferably a polyolefin, i.e. a polymeric 1-olefin or a copolymer of two or several different 1-olefins. 1-Olefins preferably include compounds of the formula I $$R-CH=CH_2 \quad (I)$$

in which R is hydrogen or alkyl with 1, 2, or 3 carbon atoms. Suitable poly-(1-olefins) include especially polyethylenes of high or of low density (HDPE and LDPE), polypropylene (PP) and ethylene-propylene-copolymers (APC). Terpolymers of two different 1-olefins and one unconjugated diene having at most 10 carbon atoms (APTC) are also appropriate, examples of suitable dienes being hexadiene-(1,4), dicyclopentadiene and ethylidene norbornene. A partially halogenated, preferably chlorinated, polyolefin, especially a chlorinated polyethylene (CPE) may also be considered as a polyolefin within the scope of the present invention. The substrate polymer may alternatively be a mixture of various polyolefins, for example a PE/CPE mixture.

The polymer substrate usually has an average molecular weight (weight average) of from 50,000 to 2,000,000, preferably of from 100,000 to 1,000,000.

The polymer substrate is grafted with a vinyl monomer according to the invention, which monomer possesses an oxygen, sulfur, fluorine and/or nitrogen atom-containing functional group. This functional group preferably is a hydroxy group, a sulfonic acid group, a fluoroalkyl ester group or an alkylamide group. A vinyl monomer which is particularly suitable is a N-vinylalkylamide of the formula II

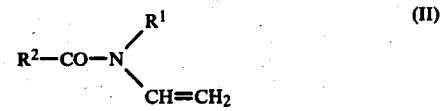

in which $R^1$ and $R^2$ are identical or different and each represent hydrogen or alkyl having from 1 to 6, preferably 1, 2 or 3 carbon atoms; an acrylic acid ester of the formula III $$CF_3-(CF_2)_x-(CH_2)_y-O-CO-CH=CH_2 \quad (III)$$

in which x is an integer from 3 to 16, preferably 6 to 12, and y is an integer from 1 to 12, preferably 2, 3 or 4, or a vinylidene carbonate of the formula IV

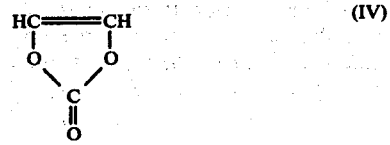

or a vinylsulfo compound of the formula V $$X-SO_2-CH=CH_2 \quad (V)$$

in which X is a halogen atom, preferably a chlorine atom, a hydroxy group or the group OMe with Me being an alkali metal atom, are further suitable vinyl monomers.

Suitable N-vinylalkylamides are, for example N-vinyl-formamide, N-vinyl-acetamide, N-vinyl-N-methyl-acetamide, N-vinyl-propionic acid amide, N-vinyl-N-methyl-propionic acid amide, N-vinyl-butyric acid amide and N-vinyl-N-methyl-butyric acid amide. Suitable acrylic acid esters of the formula III are, by way of example, 2-(perfluoro-n-butyl)-ethyl-acrylate, 2-(perfluoro-n-pentyl)-ethyl-acrylate, 2-(perfluoro-n-hexyl-ethyl-acrylate, 2-(perfluoro-n-heptyl)-ethyl-acrylate, 2-(perfluoro-n-octyl)-ethyl-acrylate, 2-(perfluoro-n-nonyl)-ethyl-acrylate, 2-(perfluoro-n-decyl)-ethyl-acrylate, 2-(perfluoro-n-undecyl)-ethyl-acrylate and 2-(perfluoro-n-dodecyl)-ethyl-acrylate and the corresponding derivatives of n-propylacrylate and n-butylacrylate.

As vinylsulfo compounds, vinylsulfonic acid and vinylsulfonic acid derivatives, especially vinylsulfohalides and alkali metal salts of vinylsulfonic acid, for example vinylsulfobromide, vinylsulfochloride, and the sodium and the potassium salt of vinylsulfonic acid, may be used. It may be particularly advantageous to graft several different vinyl monomers, which either belong to a defined monomer group or to various of the aforementioned monomer groups, onto the polymer substrate. Additionally any further vinyl monomers which can be copolymerized may be used as graft components, in addition to the particular vinyl monomers according to the invention, since this frequently facilitates the graft reaction. Suitable compounds for this purpose are, by way of example, vinyl halides, vinyl esters of monobasic aliphatic carboxylic acids having of from 2 to 12 carbon atoms, acrylic acid or methacrylic acid esters of monovalent alkanols having of from 1 to 4 carbon atoms and acrylonitrile, in an amount of from 30 to 70 weight percent, calculated on the total monomer quantity.

The graft polymer is obtained by grafting at least one vinyl monomer onto the polymer substrate under known conditions, either in the presence of a free radical-forming initiator or by means of radiation of high energy, with the exclusion of atmospheric oxygen under an inert gas atmosphere, nitrogen being the preferred inert gas. A suitable initiator is a peroxy compound, tertiary butyl esters of monobasic carboxylic acids having from 1 to 8 carbon atoms, for example tertiary butyl peracetate, dibenzoylperoxide, dilauryl peroxide, diisopropyl percarbonate, tertiary butyl perbenzoate, tertiary butyl peroctoate diteriary butyl peroxide, and cumene hydroperoxide being prerferred. The quantity of the initiator ranges from 0.01 to 10 weight percent, preferably from 0.1 to 2 weight percent, calculated on the total quantity of the vinyl monomers employed. The initiator is either added to the reaction mixture in the required amount or free radicals are produced in the reaction mixture by means of radiation of high energy. In the latter case, the dose rate of the radiation is in the range from 50 to 100,000 J/kg, preferably from 100 to 50,000 J/kg. γ-rays are preferably employed, for example using a 60 Co-source. The graft operation is generally carried out at a temperature from 0° to 100° C., preferably from 20° to 80° C., optionally in the presence of a solvent for the monomer and optionally in the presence of molecular weight regulating substances.

The product obtained in the above described graft reaction generally consists of a mixture of the real graft polymer, the polymer substrate employed and the homo- or copolymer of the vinyl monomer or of the corresponding vinyl monomer mixture. The composition of this polymer mixture depends in the first place on the nature of the polymer substrate and of the vinyl monomer and on the reaction conditions, for example temperature, reaction medium, initiator etc.

Mixtures of the above polymers may also be used according to the invention, especially in the case where the homo- or co-polymer of the vinyl monomer or of the corresponding vinyl monomer mixture is not soluble in water or is slightly water-soluble. This is the case for example when vinyl monomers of the formula III are used alone or are the main components of the reaction mixture.

According to a preferred embodiment of the process of the invention, the homopolymer of the corresponding vinyl monomer obtained during the graft reaction as a by-product is substantially separated from the graft copolymer obtained, preferably by washing with a suitable solvent. This solvent must be capable of dissolving both the vinyl monomer and the homopolymer, but not the polymer substrate and the desired graft polymer. These latter are only allowed to swell slightly under the influence of the solvent. The quantity and the nature of the solvent depend on the polymer substrate and the vinyl monomer used in each case. Suitable solvents are, for example, aromatic hydrocarbons, for example toluene, lower alkanols, for example ethanol and isopropanol, aliphatic halogenohydrocarbons, for example, 1,2,2-trichloro-1,1,2-trifluoroethane, and water. The quantity of the solvent is generally one to five times the total weight of the vinyl monomers used. This extraction in solution makes it possible to keep the quantity of homo-(co)-polymer of the vinyl monomer (mixture of vinyl monomers), at least at the surface of the plastics material or of the article prepared therefrom, at a level below 10 weight percent, preferably of from 1 to 0.1 weight percent, calculated on the total polymer mixture. The quantity of polymer substrate in the grafted plastics material or in the article grafted at the surface is generally of from about 50 to 99.99 weight percent, preferably of from about 90 to 99 weight percent, calculated on the total polymer mixture. The corresponding value for the surface area only is in most cases smaller than 40 weight percent, preferably it is from 1 to 30 weight percent.

By the term "surface" there is to be understood preferably a zone which reaches up to a depth of about 1 micron, although for the intended purpose of the invention, a graft up to a depth of a few Angströms, which may be measured for example by the change of the surface tension, will be sufficient.

The essential feature of the plastics materials according to the invention is that at least its surface, which comes into contact with the blood, is treated in a way to have athrombogenic properties. The same applies to molded articles which are used biomedically. These articles may generally be prepared in two different ways according to the invention, (1) for example by thermoplastic molding of the plastics material according to the invention by the usual processes, for example by molding, injection molding, extrusion and blow molding or (2) by a usual thermoplastic molding of the polymer substrate, which after molding may be rendered dimensionally stable by cross-linking of the polymer, and by subsequent grafting of a vinyl monomer onto the surface of the polymer substrate of the molded article, the shape of the latter remaining unchanged.

In order to avoid decomposition during the processing according to (1), it is generally advisable to add stabilizers. For this purpose, only physiologically tolerable stabilizers, for example calcium, magnesium, aluminum and zinc salts of fatty acids, organic phosphites, aliphatic epoxides, polyhydric alcohols and phenolic antioxidants should be used. A stabilizer combination consisting of from 1 to 3 weight percent of calcium-aluminum stearate, 0.5 to 1 weight percent of a secondary or tertiary organic phosphite, 1 to 3 weight percent of an aliphatic epoxide and 0.05 to 10 weight percent of a phenolic antioxidant, calculated on the plastics material, has proved particularly advantageous. Furthermore usual light-stabilizers, lubricants, pigments and fillers, for example barium sulfate as a contrast medium for radiographic purposes, may be used.

The additives may be incorporated into the plastics material during its preparation or thereafter.

The plastics material according to the invention, which is usually obtained in the form of a powder or of granules, serves for the preparation of any objects which partially or completely replace organs of homothermal beings or which are used for storing, examining, or treating blood or blood plasma. Examples thereof are rods, threads, sheets, flexible tubes, tubes, bags, plates, balls, sieves, grids, nets, fibers and hollow fibers.

In most cases the mechanical resistance of these objects is sufficient for the intended purposes. In some cases, however, it may be advantageous to improve the mechanical resistance thereof by incorporating a supporting web of mineral or organic material, for example glass fibers or plastics fibers, for example made of polyester or polyamide. In this case it is also possible to use sandwich sheets, the inner sheet, which comes into contact with blood or with blood plasma, consisting of the plastics material according to the invention and consequently, acting as a lining, and the outer sheet being made of a material which is particularly resistant mechanically.

The blood tolerance (athrombogenic property) is defined as the property of a material to behave neutrally towards the coagulation systems contained in the blood, i.e. not to cause small coagula(thrombi). As a general rule, heterogenous material acts both on the cellular and on the plasma blood constituents, the action on the coagulation factors II, IX, XI and XII being particularly important. The coagulation factors are generally determined according to the method of Hardisty and Mcpherson [cf. Thromb. Diath. Haemorrh. 7, 215 (1962)].

The blood tolerance of the plastics material according to the invention is determined by a series of tests, the sum of the results of which permits a statement about the blood tolerance. The plastics material to be tested is either used in the form of small balls (ball test) or in the form of a tube (tube test) according to whether the polymer substrate used is a relatively hard material, for example PP or a relatively soft material, for example APTC.

For the purpose of the ball test, human blood plasma is used which has been obtained by centrifugation (3,000 g; 20 minutes) of human whole blood and to which 10 volume percent of a 3.8 weight percent aqueous sodium citrate solution has been added in order to prevent coagulation. The plastics material is present in the form of small balls of a diameter of 0.2 to 0.3 mm and the total surface of the sample has a dimension of 110 cm$^2$. To the plastics material, which is placed in a polystyrene tube, 1 ml of blood plasma is added and after closure of the tube the test material is incubated while stirring at a temperature of 37° C. The activities of the coagulation factors II, IX, XI and XII are determined after 30, 60, 120 and 240 minutes respectively. A comparative test is carried out under the same conditions in the absence of the plastics material. The coagulation activities, expressed in percent of the results of the comparative test, are integrated over the incubation times, and the integration values of the individual measures are summed. The value thus obtained (percent activity per minute) is a measure for the influence of the plastics material on the blood plasma, the influence being the smaller, the smaller the value.

For the purpose of the tube test, human whole blood is used to which 10 volume percent of a 3.8 weight percent aqueous citrate solution has been added. The plastics material is used in the form of a tube having a length of 75 cm and an inner diameter of 5 mm. The tube is filled with 10 ml of blood and thereafter the tails of the tubes are closely linked with one another. The tube is bent to form a circle and is fixed onto a rotary plate having an inclination of 75° C. The rotary plate rotates for 2 hours at 15 revolutions per minute at a surrounding temperature of 37° C. Thereafter the number of the platelets is determined using a commercial particle counter (manufacturer: Coulter Electronic Ltd.). Thereafter the cellular constituents of the blood are removed by centrifugation (3000 g, 20 minutes) and with the resulting blood plasma the following parameters are determined:

(a) platelet factor 3 [according to Hardisty and Hutton, Brit. J. Haemat., 11, 258 (1965)];

(b) platelet factor 4 [according to Harada and Zucker, Thromb. Diath. Haemorrh., 25, 41 (1971)];

(c) recalcification time: To 0.2 ml of the plasma 0.2 ml of an aqueous calcium chloride solution (0.025 molar) is added at a temperature of 37° C. and the time until coagultion occurs is determined using a commercial automatic coagulometer;

(d) partial thromboplastin time: 0.1 ml of a thromboplastin reagent (manufacturer: Behringwerke AG, Germany) is pipetted to 0.1 ml of the plasma at a temperature of 37° C. and the test mixture is incubated for 2 minutes. Thereafter 0.1 ml of an aqueous calcium chloride solution (0.025 molar) which has been preheated to 37° C. is added and the time until coagulation occurs is determined with a commercial automatic coagulometer;

(e) coagulation factors II, IX, XI and XII.

All the measured values are calculated on the initial values of the untreated blood or plasma. The deviations in percent from the initial values are added and divided by the number of the measured parameters. The value obtained in this process (in percent) is a measure for the influence of the plastics material on the blood, the influence being the smaller the smaller the value.

The following examples illustrate the invention. The abbreviations used have the following meanings:

LDPE: polyethylene of low density with MFI(190/5) 2 g/10 min. (according to German Industrial Standard DIN 53 735)

HDPE: polyethylene of high density with
MFI(190/5) 1.6 g/10 min. or
MFI(190/5) 0.5 (according to Example 15)

PP: polypropylene with MFI(190/5) 3 g/10 min.

CPE: chlorinated polyethylene with CI content of 39 percent and average molecular weight of 220,000

APTC: terpolymer of 69.7 weight percent of ethylene, 25 weight percent of propylene and 5.3 weight percent of ethylidene norbornene having a viscosity of 85 Mooney ML 1+4 (100° C.) (according to DIN 53 523)

VF: N-vinylformamide

VIMA: N-vinyl-N-methyl-acetamide

VICA: vinylidene carbonate

FA: mixture of
  5 weight percent of 2-(perfluoro-n-pentyl)-ethyl-acrylate,
  50 weight percent of 2-(perfluoro-n-heptyl)-ethyl-acrylate, 30 weight percent of 2-(perfluoro-n-nonyl)-ethyl-acrylate,
15 weight percent of 2-(perfluoro-n-undecyl)-ethyl-acrylate,
VSCl: vinylsulfochloride
VSNa: sodium salt of vinylsulfonic acid
AN: acrylonitrile
DMF: dimethylformamide
TTE: 1,2,2-trichloro-1,1,2-trifluoroethane
EA: acetic acid ethyl ester
BPO: tertiary butylperoctoate
BPAc: tertiary butylperacetate

EXAMPLES 1 to 4

In each of the examples 100 g of a polymer substrate are introduced into a 1 liter flask with stirrer and the flask is freed of air by passing nitrogen through. The previously purified liquid monomer is added and to the mixture the initiator is added. The mixture is stirred for a certain period whereupon the polymer substrate swells slightly (swell time). Thereafter the mixture is heated to a polymerization temperature of 65° C. and this temperature is maintained for a certain period (polymerization period) while stirring. After cooling to room temperature, washing liquid is added to the reaction mixture and the pulverulent graft polymer is suction-filtered and washed repeatedly with washing liquid. The polymer powder obtained is dried for 24 hours at a temperature of 60° C. under a pressure of 130 mbars. The dried graft polymer is sieved and the sieve fraction having a granular size of from 0.2 to 0.3 mm is submitted to a blood test (ball test). Details and results may be seen from table 1.

The graft polymer obtained according to Example 3 is hydrolyzed prior to drying with an aqueous sodium hydroxide solution of 8 weight percent strength.

EXAMPLES 5 to 10

In each of the examples 100 g of a polymer substrate are introduced into a Schlenk tube serving as reaction vessel and the vessel is rinsed with nitrogen. After evacuation of the vessel, the previously purified monomer, optionally in admixture with a solvent, is introduced into the vessel under reduced pressure and the reaction mixture is blanketed with nitrogen. After expiration of a predetermined swell time, the vessel is exposed for a certain period to γ-radiation produced by a 60-Co-source, at a temperature of 25° C. (polymerization time). Thereafter the mixture is washed with washing liquid and the pulverulent graft polymer is suction-filtered and repeatedly washed with washing liquid. Drying, sieving and the blood test are carried out analogously to Examples 1 to 4. Details and results concerning these examples may be seen from table 2.

The graft polymer obtained according to the Examples 7 to 10 is hydrolyzed prior to drying with isopropanolic sodium hydroxide solution of 8 weight percent strength.

EXAMPLES 11 to 22

A tube of circular cross-section, of 75 cm length and of 5 mm inner diameter, is produced by extrusion from the polymer substrate in each case. The tube is rinsed with nitrogen, completely filled with the corresponding vinyl monomer or monomer mixture, optionally together with a solvent, and the tube is hermetically closed under a nitrogen atmosphere. The tube is then exposed to γ-radiation generated by a 60-Co-source after having been placed into a vessel filled with nitrogen, at a temperature of 25° C. Upon completion of the radiation, the tube is emptied, repeatedly washed with washing liquid and dried analogously to the Examples 1 to 4. Thereafter the tube material is submitted to a blood test (tube test). Details and results concerning these Examples may be seen from table 3. The indications in percent under "monomer", "comonomer" and "solvent" are calculated on the total weight of these components.

When using APTC as polymer substrate, the tube is additionally briefly exposed to γ-radiation ($2.10^4$ J/kg) prior to grafting the vinyl monomer.

Table 1

| Example | 1 | 2 | 3 | 4 |
|---|---|---|---|---|
| substrate | LDPE | PP | PP | PP |
| monomer | VIMA | VIMA | VIMA | VICA[1] |
| quantity (g) | 400 | 400 | 400 | 145 |
| initiator | BPO | BPO | BPAc | BPO |
| quantity (g) | 5 | 2 | 5 | 4.35 |
| swell time (h) | 4 | 3 | 3 | 1.5 |
| polymerization time (h) | 1.33 (h) | 1 | 1 | 5 |
| washing liquid | methanol | methanol | methanol | DMF |
| graft degree | 0.32 | 1.5 | 0.4 | 0.05 |
| ball test value | 153 | 122 | 106 | 55 |

Table 2

| Example | 5 | 6 | 7 | 8 | 9 | 10 |
|---|---|---|---|---|---|---|
| substrate | PP | PP | PP | PP | PP | PP |
| monomer | VIMA | VICA | VICA[1] | FA | VSCl | VSCl[1] |
| quantity (g) | 100 | 100 | 100 | 40 | 250 | 160 |
| solvent | — | — | — | toluene | — | — |
| quantity (g) | | | | 160 | | |
| radiation dose ($10^{-4}$ J/kg) | 0.5 | 4 | 4 | 0.1 | 4 | 2 |
| swell time (h) | 3 | 3 | 3 | 3 | 3 | 3 |
| polymerization time (h) | 4 | 32 | 32 | 0.8 | 32 | 16 |
| washing liquid | methanol | DMF | mrthanol | TTE | EA | water |
| graft degree | 4 | 0.9 | 0.9 | 1.83 | 1[2] | 1[2] |
| ball test value | 95 | 112 | 95 | 74 | 77 | 72 |

[1] hydrolyzed
[2] determined by elementary analysis: in comparison: The ball test values of the untreated polymer substrates were 228 for LDPE and 179 for PP.

Table 3

| Example | 11 | 12 | 13 | 14 | 15 | 16 |
|---|---|---|---|---|---|---|
| substrate | APTC | PP | HDPE | LDPE | HDPE/ | APTC |

Table 3-continued

| Example | 11 | 12 | 13 | 14 | 15 | 16 |
|---|---|---|---|---|---|---|
| | | | | | CPE(4:1) | |
| monomer | VIMA | VIMA | VIMA | VIMA | VIMA | FA |
| portion (%) | 100 | 100 | 100 | 50 | 50 | 50 |
| solvent | — | — | — | toluene | toluene | toluene |
| portion (%) | | | | 50 | 50 | 50 |
| radiation dose ($10^{-4}$ J/kg) | 0.5 | 0.5 | 0.5 | 0.5 | 1 | 0.01 |
| swell time (h) | 3 | 3 | 3 | 3 | 3 | 3 |
| polymerization time (h) | 4 | 4 | 4 | 4 | 8 | 0.03 |
| graft degree | 5 | 5 | 0.5 | 5 | 5 | 1 |
| tube test value | 13 | 7 | 14 | 15 | 19 | 22 |
| Example | 17 | 18 | 19 | 20 | 21 | 22 |
| substrate | APTC | APTC | APTC | APTC | APTC | APTC |
| monomer | FA | VIMA | VIMA | VF | VIMA | VSNa |
| portion (%) | 50 | 40 | 25 | 100 | 90 | 20 |
| comonomer | — | FA | FA | — | VSNa | AN |
| portion (%) | | 10 | 25 | | 10 | 20 |
| solvent | toluene | TTE | toluene | — | — | water |
| portion (%) | 50 | 50 | 50 | | | 60 |
| radiation dose ($10^{-4}$ J/kg) | 0.005 | 0.01 | 0.02 | 0.02 | 0.2 | 0.5 |
| swell time (h) | 3 | 3 | 3 | 3 | 3 | 3 |
| polymerization time (h) | 0.04 | 0.08 | 0.16 | 0.16 | 1.6 | 4 |
| graft degree | 0.8 | 1.7 | 7-14 | 0.5 | 2.7/2[a)] | 1[a)]/7[a)] |
| tube test value | 10 | 10 | 18 | 19 | 10 | 18 |

[a)]determined by elementary analysis in comparison: The tube test values of the untreated polymer substrates were 26 for APTC and LDPE, 30 for PP and 28 for HDPE/CPE

What is claimed is:

1. A plastics material, adaptable to biomedical uses, the surface of which material at least partially consists of a graft copolymer having a hydrocarbon main chain and side chains grafted thereon, said side chains being polymers comprising at least one vinyl monomer selected from the group consisting of vinylene carbonate and N-vinyl alkylamides of the formula

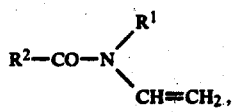

wherein $R^1$ and $R^2$ are the same or different and each is hydrogen or alkyl having 1 to 6 carbon atoms.

2. A plastics material as in claim 1 wherein the polymers of said side chains additionally comprise vinyl monomers other than said vinylene carbonate or N-vinyl alkylamides.

3. A plastics material as in claim 1 wherein said hydrocarbon main chain is a polyolefin.

4. A plastics material as in claim 2 wherein said polyolefin has a weight average molecular weight from 50,000 to 2,000,000.

5. A plastics material as in claim 1 wherein aid graft copolymer has a graft degree from 0.01 to 80 percent.

6. A shaped article for biomedical use consisting essentially of a plastics material as in claim 1.

7. A shaped article for biomedical use, surface portions of which article consist of a plastics material as in claim 1.